United States Patent [19]
Hanson

[11] 3,993,743
[45] Nov. 23, 1976

[54] METHOD FOR DIAGNOSIS OF CHAGAS' DISEASE

[75] Inventor: William L. Hanson, Bishop, Ga.

[73] Assignee: Research Corporation, New York, N.Y.

[22] Filed: Feb. 7, 1975

[21] Appl. No.: 547,956

Related U.S. Application Data

[62] Division of Ser. No. 386,285, Aug. 7, 1973, Pat. No. 3,911,097.

[52] U.S. Cl. .................................. 424/12; 424/85; 424/88
[51] Int. Cl.² ................. G01N 31/02; G01N 33/16; A61K 39/00
[58] Field of Search .......................... 424/12, 85, 88

[56] References Cited
OTHER PUBLICATIONS

Bergendi, Chem. Abs., vol. 74, 1971 p. 175, No. 11475n.

Capron, Chem. Abs., vol. 71, 1969 p. 186, No. 79194p.

*Primary Examiner*—Albert T. Meyers
*Assistant Examiner*—A. P. Fagelson
*Attorney, Agent, or Firm*—James C. Haight

[57] ABSTRACT

A process for diagnosing Chagas' disease in a living mammal susceptible to infection by *Trypanosoma cruzi* which comprises reacting in vitro an antibody-containing blood sample from said mammal in an immunoprecipitin test with an immunologically effective amount of a purified water-soluble antigen extract obtained from essentially only the trypomastigote and amastigote growth stages of the protozoa *Trypanosoma cruzi*, and diagnosing the presence of Chagas' disease from the formation of precipitin bands at an antigen-antibody interface.

5 Claims, No Drawings

METHOD FOR DIAGNOSIS OF CHAGAS' DISEASE

This is a division of application Ser. No. 386,285, filed Aug. 7, 1973, now U.S. Pat. No. 3,911,097.

This invention may be manufactured and used for the Government of the United States of America for governmental purposes without the payment of any royalties therefor.

This invention relates to a diagnostic reagent for Chagas' disease. More particularly, this invention relates to an antigenic preparation suitable for use in immunoprecipitin diagnostic tests for both acute and chronic Chagas' disease.

Trypanosomes are osmotrophic protozoa which are frequently parasitic in vertebrates, developing in the bloodstream where they absorb nutrients from the infected host. Infections are readily transmitted via intermediate insect vectors. The American *Trypanosoma cruzi* causes Chagas' disease which is endemic in several countries of Central and South America, especially Mexico, Brazil, Chile, Argentina and Venezuela, as well as in parts of the southern United States. Common vertebrate hosts include man, household pets, e.g. dogs and cats, and wild mammals, e.g. bats, certain monkeys and oppossums. Because the organisms are easily transmitted by the common reduviid bugs, the incidence of human infections by virulent *T. cruzi*, is very high. The World Health Organization estimated in 1970 (WHO Scientific Publication No. 195) that at least seven million people in Latin America are infected with *T. cruzi*, with another 35 million persons exposed to infections by this parasite.

Chagas' disease is especially dangerous because at the present time there are no satisfactory prophylactic or curative therapeutic agents available, and because, as far as is known, once the disease is contracted by a patient, the individual remains infected until death. While *T. cruzi* is transmitted to man and animals naturally by blood sucking bugs, transmission by blood transfusion has become the second most important means of transmission in recent years. It has been estimated that some 8 million units of blood are processed annually by blood banks in the United States alone. While it is obviously desirable to exclude people having *T. cruzi* antigen as determined by axenic culture from donating blood, many potential donors could possess antibodies to *T. cruzi*, but not the antigen in detectable quantities. Theoretically, these persons may carry an antigen-antibody complex that could be infectious. For this reason, it would be desirable to screen donated blood in or from endemic areas for the presence of both antigens and antibodies.

A number of different morphological stages of *T. cruzi* are known to exist depending on the environment in which they occur. The morphological stages that occur in the body of the infected mammal are the trypomastigote and amastigote stages. When these forms are placed into in vitro axenic culture or are ingested by the insect vector, they change into a third type called the epimastigote. This latter stage is relatively easily grown and has been utilized for many years in the production of antigen for studies involving immunization as well as for diagnostic procedures.

The most common procedures heretofore available for diagnosis of Chagas' disease in patients or for monitoring blook banks are xenodiagnosis (feeding laboratory-reared kissing bugs on the suspected patient and checking the insects later for the presence of parasites), various in vitro culture techniques, and immunological procedures. These techniques have been reviewed by Goble in "Immunity to Parasitic Animals", Vol. II, pp 597–689, Appleton-Century-Crofts, N.Y., 1970, the contents of which are incorporated by reference herein. The former two procedures suffer many disadvantages, and generally require a wait of from several days to several weeks before the test results are known. Important limitations of the immunological procedures currently used (complement fixation, fluorescent antibody and indirect hemagglutination) are that the procedures generally are time-consuming and require a fairly high level of technical skill and equipment for satisfactory results, the availability of which is limited in many parts of the western hemisphere where Chagas' disease is endemic. A very significant limitation of immunoprecipitin procedures currently in use and mentioned by Goble is that, while the test is reasonably sensitive for the acute stages of Chagas' disease, the sensitivity of this procedure with antigen from epimastigotes is not satisfactory for diagnosis of chronic Chagas' disease. Accordingly, there is great need for a simple, inexpensive, rapid, specific and sensitive method for diagnosis of Chagas' disease.

Because of the present lack of effective chemotherapeutic treatment for Chagas' disease, several attempts have been made to develop vaccines effective for immunization and the production of diagnostic and protective antibodies. Vaccines and other antigenic preparations which have been used with the African Sleeping sickness-causing trypanosomes are unsuitable for use with the American *T. cruzi* which is a morphologically, biologically, pathologically and immunologically distinct protozoa; indeed, many workers prefer to refer to *T. cruzi* as *Schizotrypanum cruzi*. *T. cruzi* vaccines have heretofore been prepared from the epimastigote stage present in axenic culture and in the insect vector, or from immunologically related protozoa, e.g. as described in British Pat. Nos. 723,708 and 1,099,463.

Neal's article in Nature, No. 4901 at page 83 (Oct. 5th, 1963), indicates the existence of a *T. cruzi* antigen in the plasma of mice heavily infected with the trypanosomes and which gives some protection against challenge when whole plasma or serum is injected with an adjuvant into test animals of the same species. Such blood fractions are unsuitable for either the diagnosis of Chagas' disease or for immunizing species different from the host species from which the plasma is collected, since the infected animal from which the blood fraction is obtained is itself likely to contain antibodies to the *T. cruzi* antigen as well as a spectrum of other antibodies and antigens which render such fractions highly non-specific and particularly unsatisfactory for diagnostic use. This article further indicates that the crithidial or epimastigote forms of *T. cruzi* grown in vitro and the culture medium therefrom have a considerable protective effect against challenge; however, as previously indicated herein, such antigens are unsuitable for the diagnosis of chronic Chagas' disease.

It is known that the trypomastigote and amastigote stages of *T. cruzi* can be produced in the laboratory by growing the parasite in tissue culture preparations, including both primary diploid cell cultures and continuous haploid cell lines. For example, Thompson et al reported in J. Protozo, 13 (1): 110 (February, 1966), on the growth of *T, cruzi* in primary chick embryo cell cultures, while Neva et al in Am. J. Trop. Med. Hyg. 10

(2): 140 (March, 1961), Cantella et al in Proc. 2nd Int'l Cong. Parasit. (Part 4, 8, 1971) and others have described experimental growth of *T. Cruzi* in the HeLa cell line. Limited quantities of the parasite can be obtained by these methods, but suitable quantities of such preparations for practical uses on a wide scale have not heretofore been reported.

OBJECTS OF THE INVENTION

It is a general object of the invention to provide an improved diagnostic reagent suitable for immunochemical detection of Chagas' disease.

Another object of this invention is to provide a method for the rapid detection of both acute and chronic Chagas' disease in infected mammalian hosts.

A further object of the present invention is to provide a highly specific and sensitive immunoprecipitin antigen useful in the detection of Chagas' disease.

An additional object of this invention is to provide an effective vaccine against Chagas' disease.

A more particular object of the present invention is to provide an immunoelectro-osmophoretic test and kit for the detection of Chagas' disease.

Upon further study of the specification and appended claims, further objects and advantages of this invention will become apparent to those skilled in the art.

SUMMARY OF THE INVENTION

Briefly, the above and other objects are attained in one aspect of the present invention by providing a process

DETAILED DISCUSSION

According to the present invention, antigenic preparations from the trypomastigote and/or amastigote stages, preferably the former, of *T. cruzi* are employed for immunological vaccination and diagnostic procedures, particularly for immunoprecipitin testing. While not wishing to be bound by any theory of the present invention, it is postulated herein that greatly improved antigenic preparations can now be prepared therefrom due to the known fact that *T. cruzi* undergoes in vivo transformation in the vertebrate host from the epimastigote to the trypomastigote and amastigote stages and is thus used in accordance with the present invention in the same stages which occur in the infected mammalian host.

In accordance with one aspect of the present invention, it has been found that the trypomastigote and amastigote stages of *T. cruzi* grown in tissue culture host cells possess antigens which can be separated and purified from cellular material and nutrient medium containing metabolic products to form a water soluble antigen preparation useful in immunoprecipitin testing and as a vaccine. Since the antigen of the present invention is water soluble, it is suitable for the use in gel diffusion techniques and can be sterile filtered. Because it is antigenic, yet free of *T. cruzi* organisms, vaccines prepared therefrom do not pose the danger of *T. cruzi* infections.

While *T. cruzi* can be grown in primary cell cultures, e.g. chick embryo, bovine embryonic muscle, and embryonic avian tissue, it is preferred to use a continuous established cell line in order to minimize the variables encountered in production. In principle, any tissue culture susceptible to infection by *T. cruzi* can be used. While the HeLa cell line has been used almost exclusively for this purpose in the past, it has surprisingly been discovered that the Vero cell line produces approximately a fivefold increase in the number of parasites obtained in comparison with HeLa. Other tissue cultures susceptible to infection by *T. cruzi* can be used, e.g., embryonic rat skin muscle, human embryonic skin, muscle, heart, lung, chicken macrophages, and bovine embryonic kidney, but generally give lower yields than obtained even with HeLa.

Viable *T. cruzi* can be inoculated into the tissue culture from any convenient source, e.g. from clinical isolates, axenic cultures, animal or tissue culture passages of isolates, of from standardized strains such as ATCC 30013; the experiments reported herein employed the Brazilian (Goble) strain obtained in 1967 from Dr. P. E. Thompson, Parke-Davis Company, Ann Arbor, Michigan. The particular *T. cruzi* strain utilized is not critical and forms no part of the present invention. The inoculant can be in any morphological form, even purely epimastigote, since transformation to the trypomastigote and amastigote stages take place spontaneously during tissue culture cultivation, as has been reported by Rodriguez and Marenkelle in Expt. Parasitol. 27: 78–87 (1970). The inoculated tissue culture can be either a monolayer or a suspension, but confluent monolayers are preferred due to the relative ease of harvesting the protozoa therefrom. The inoculated culture is incubated under cellular growth conditions, i.e., with a suitable nutrient medium in a sealed container and at a slightly elevated temperature, generally of 30°–42° C, preferably about 35°–37° C.

The only requirement of the nutrient medium is that it be capable of supporting growth of the particular tissue culture cell line susceptible to infection by *T. cruzi;* many such media are known to those skilled in the art. Generally a growth-promotant free of *T. cruzi* antibodies, e.g. fetal calf serum, will be added in growth-promoting amounts, e.g. 1–20% by volume. Suitable nutrient media for the Vero cell line (a continuous heteroploid cell line originally derived from an African Green monkey kidney) are known in the art and include but are not limited to Eagle's MEM supplemented with 2–10% fetal calf serum and 10% tryptose phosphate broth. The maintenance medium is preferably buffered to a pH above 7.0, especially pH 7.4–7.6, to form predominantly the trypomastigote stage which forms a preferred water soluble antigen. While an initial pH of 6.6 forms 70–80% amastigotes, at an initial pH of 7.0, more trypomastigotes are formed, and at an initial pH of 7.4–7.6, 60–80% trypomastigotes are formed.

Conveniently, inoculation is effected with about $10^6$ parasites added to each 250 ml culture flask confluent monolayer. The flasks are then incubated for absorption of the protozoa from 4–24 hours at 37° C, the medium discarded, and the monolayer washed with fresh culture medium. Fresh maintenance medium containing 2–5% fetal calf serum is subsequently added and changed at 2–3 day intervals.

The yield of trypomastigotes will vary depending on the stage inoculated and the number of days of growth in tissue culture. Since epimastigotes transform into trypomastigotes in tissue culture, it is advisable to continue culturing until there are essentially only the trypomastigote and amastigote stages, i.e. less then 1–5% of the organisms remain in the epimastigote stage. This degree of transformation is generally obtained within 4–5 days. Five to ten days after inoculation of the flasks with parasites, the medium contains significant numbers of trypomastigotes and amastigotes. pH 7.4 results in 70–80% trypomastigotes and pH 7.6 results in 75–80%, the balance being essentially only amastigotes. The cultures when harvested are substantially free, i.e., they contain less than about 1% of epimastigotes.

The parasites are collected by centrifugation on alternate days from each flask for a period of approximately one month. The medium from several flasks is pooled, the parasites harvested by high speed centrifugation in a refrigerated centrifuge and repeatedly washed to remove residual media and metabolic products followed by centrifugation with a balanced salt solution. The parasites are subsequently stored frozen in a sterile neutral balanced salt solution e.g. at pH 6.5–7.5, until a desired quantity is accumulated. The organisms are subsequently disrupted to release soluble antigen, e.g. by sonication or homogenizing in an ultra high speed blender. The disrupted material is then centrifuged and/or sterile filtered and the soluble supernate or filtrate recovered, and aliquots are stored frozen until ready for use. This supernate serves as the antigen for vaccination of experimental animals and for immunoprecipitin diagnostic procedures. One advantage of the present invention is that, while further purification of the antigens can be effected if desired, such additional steps are generally unnecessary to provide a useful antigen preparation.

The supernate thus collected has a protein content of 0.1–10 mg per ml, generally of 1–5 mg per ml as determined by the Folin-phenol method of Lowry et al, J. Biol. Chem. 193: 265 (1951), and can be concentrated or diluted as desired by known techniques. Because of the manner of preparation according to the present invention, the supernate is substantially free of serum proteins, particularly serum protein antibodies. Although trace amounts of growth promotant can be tolerated and protein released by the disruption of the *T. cruzi* and residual tissue culture cells will be present in unpurified preparations, the antigen preparation is substantially free of serum protein antibodies, i.e. they constitute less than about 1% of the total protein in the supernate. No change in the immunological activity of the antigen has been noted after six months storage frozen at −20° C, and it can be lyophilized without loss of activity.

For the preparation of vaccines suitable for immunizing animals against the trypomastigote and amastigote stages of *T. cruzi*, either for protection against challenge or to prepare diagnostic antibodies in laboratory animals, conventional vaccine preparation techniques can be used. Preferably a non-antigenic adjuvant, e.g. alum, Freund's complete adjuvant, saponin, a quatenary ammonium surfactant, an alkyl amine, etc. is admixed with the supernatant in a suitable pharmaceutically acceptable non-antigenic carrier and the resultant mixture sterilized, e.g. by filtration.

The vaccine can be administered parenterally following regimens already known for immunization with other trypanosome vaccines, preferably followed by at least one additional injection one to six weeks later. Good results have been obtained in $CF_1$ mice using three injections of 1–5 mg protein each on alternate weeks and challenging two weeks after the last injection. The protein content per injection in mice and other mammals can be varied, but is generally 75–750 and preferably 250–500 mg of protein supernate per kg of body weight. The antibodies can be collected and worked up using methods well known to those skilled in the art of protein chemistry, and provide a useful reagent for the immunological detection of trypomastigote and/or amastigote soluble antigens in a variety of immunochemical procedures, e.g. immunoprecipitin, fluorescent antibody, serum neutralization, etc. Such antibodies are useful as a control reagent in the diagnostic test for Chagas' disease described more particularly below.

Alternatively to using the above-described antigen supernate as the immunologically active agent in a vaccine, it can be used directly without further purification as a diagnostic antigen in immunological tests for Chagas' disease. While in principle applicable to a variety of immunological tests currently in use, e.g. those described by Goble in the aforementioned text, immunoprecipitin tests represent a presently preferred embodiment and accordingly will be discussed in detail.

The simplest immunoprecipitin test involves capillary tube precipitin testing wherein separate antibody and antigen solutions are allowed to react at a common interface in a capillary tube, and a positive reaction is indicated by the formation of a precipitate at the interface. This method is relatively insensitive and inaccurate due, inter alia, to unavoidable diffusion of the two solutions across the interface, and the final test results cannot be preserved.

Agar gel diffusion is the simplest method which avoids these drawbacks. The antigen is placed in a central well punched in a continuous agar gel, and appropriate dilutions of a serum containing suspected antibodies are placed in wells concentrically surrounding the center well. A positive reaction is noted by the formation of a precipitin line between one or more of the concentric wells and the central well. This method is relatively insensitive and fairly slow, requiring one to four days to read the test results.

Radioimmunoassays, e.g. radioimmunoprecipitation tests, are extremely sensitive (by several orders of magnitude over older methods) but take several days to perform and require sophisticated equipment and highly trained personnel seldom available in areas where Chagas' disease is endemic.

Countercurrent electrophoresis is a widely used immunoprecipitin method which takes only about an hour to perform and which is considerably more sensitive than agar gel diffusion. Reactive components are placed in opposing wells cut into an agar gel, and a small electrical current is applied thereto, causing both the antigen and antibody to migrate towards each other. A positive reaction is indicated by the formation of a precipitate at the antigen-antibody interface. Disposable electrophoresis test kits are convenient to use and commercially available, e.g. the Hyland Division of Travenol Laboratories, Inc., Costa Mesa, California markets an IEOP (immunoelectro-osmophoretic) kit described in Oliva and Schultz U.S. Pat. No. 3,407,133, the contents of which are incorporated by reference herein. Since this test method and apparatus is reasonably accurate and reproducible, readily available and inexpensive, it represents the presently preferred embodiment of this aspect of the present invention.

It will be appreciated that other immunochemical methods and apparatus are, where available, equally suitable for use in the present invention.

For purposes of immunoelectrophoresis testing, the soluble antigen preparations of the present invention when used without further purification are used at a protein content of about 0.1–10 mg/ml, preferably 1–5 mg/ml, and especially about 3.5 mg per ml for IEOP testing. The limiting factor at the lower end of the range is the degree of distinction achieved in the precipitin lines, which is a function of the soluble antigen content in the total protein present. Purified antigen preparations can of course have lower total protein concentrations, and the protein content of even the unpurified preparations can be varied to suit the particular immunochemical test to be employed, the optimal amounts being determined, e.g. by testing simple serial dilutions.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

Maintenance And Production Of Parasites

Epimastigotes of a Brazil strain of *T. Cruzi* (Goble strain) were maintained and mass-produced in Yaeger's LIT medium. This medium consists of 20.0 g liver infusion broth (Difco), 5.0 g tryptose (Difco), 4.0 g sodium chloride, 0.4 g potassium chloride, 8.0 g disodium hydrogen phosphate ($Na_2HPO_4$), and 2.0 g dextrose, dissolved in one liter of glass distilled water. The pH was adjusted to 7.4, and 10 ml or 100 ml quantities were dispensed into 18 × 150 mm screw-cap tubes or 125 ml Erlenmeyer flasks respectively and autoclaved at 15 lbs pressure (121° C) for 15 minutes. 5 mg/ml hemin dissolved in 50% aqueous triethanolamine, W/V, and sterilized by filtration was added to a final concentration of 0.4%. The medium was supplemented with fetal calf serum (Microbiological Associates) to a final concentration of 5%. Epimastigotes were routinely maintained by passage every six to eight days of 0.5 – 1.5 ml from a heavily infected culture (containing approximately $4 \times 10^6$ to $1.5 \times 10^7$ parasites/ml) to fresh tubes of LIT medium. For mass-production of epimastigotes, 10 to 20 tubes or 2 to 3 Erlenmeyer flasks of medium were inoculated as described above and incubated at room temperature for 10 to 11 days. Cultures were checked for bacterial contamination by examination of a drop of medium at the time of inoculating new cultures with the aid of a phase contrast microscope. Several cultures were pooled and the parasites were harvested by centrifugation in a Sorvall RC2-B refrigerated centrifuge at 10,000 × G for 15 minutes. The supernate was discarded and the sedimented parasites were resuspended in a desired quantity of fresh LIT medium. Four microliters of the parasite suspension was placed on a slide, covered with an 18 × 18 mm coverslip, and the number of parasites per 10 fields was determined with the aid of a phase contrast microscope equipped with a calibrated ocular grid. From these counts the number of parasites per ml of culture medium was calculated and the desired dilutions were made for subsequent experiments.

*T. cruzi* was also maintained in the laboratory as trypomastigotes and amastigotes in three to four week old female $CF_1$ mice by passage of infected whole blood injected vis the intraperitoneal route every 10 to 14 days.

EXAMPLE 2

Mass Production of T. Cruzi In Tissue Culture

A study of the growth of *T. cruzi* indicated that Vero cells (continuous African Green monkey kidney cells, North American Biologicals, Rockville, Maryland) were especially efficient in the production of trypomastigotes of *T. cruzi*. The parasites are mass produced in Vero cell cultures.

To prepare the working medium, 10 ml of 10X Eagle/s MEM and 10 ml of tryptose phosphate broth (Difco) are added asceptically to bottles containing 78 ml of 1.6 g/l aqueous $NaHCO_3$ solution. 10 ml of fetal calf serum (Microbiological Associates) is added to each bottle for preparation of a growth medium, and 2 ml of fetal calf serum is added for preparation of the maintenance medium to final concentrations of 10% or 2% respectively. All media is incubated at 37° C for 2–3 days to check for sterility, then stored at room temperature until used.

Stock Vero cell cultures are maintained in Falcon tissue culture flasks (75 $cm^2$, Falcon Plastics, Los Angeles, California). To prepare new cultures in Falcon flasks, the used medium is poured off the cells and the monolayer is rinsed with 5–6 ml of 0.5% trypsin solution (prepared by dissolving 8.0 g NaCl, 0.4 g KCl, 1.0 g anhydrous granular dextrose, 0.5 g trypsin, Difco 1:250, 0.2 g versene powder and 0.58 g $NaHCO_3$ in 100 ml glass distilled deionized water). This rinsing solution is discarded and 4 ml of fresh trypsin solution is placed onto the monolayer and the flasks are incubated at 37° C for 10 minutes or until the cells detach from the flask. Eight ml. of growth medium is added, bringing the total volume of the cell suspension to 12 ml. Eight ml. of the cell suspension is removed and 4 ml is added to each of two new flasks. Fresh growth medium is then added to all flasks to a final volume of 25 ml and the cultures are incubated at 37° C. Media is removed from all flasks the following day and fresh medium added. Subsequently this is repeated every 3–4 days or when the medium pH becomes acid. Cell cultures are subcultured every 4–5 days or when flasks had heavy monolayers.

Trypomastigote stages of *T. cruzi* are mass-produced in cell production roller vessels (Bellco Glass, Inc., Vineland, New Jersey), 670 $cm^2$. Vero cell cultures are established in roller vessels from Falcon flasks. Monolayers of cells in the Falcon flasks are trypsinized as described above, and the cells of each flask are suspended in 12 ml of growth medium. Eight ml from each of two flasks is added to each roller vessel. One hundred ml of growth medium had been added to the roller vessel the previous day and incubated at 37° C for 24 hours prior to inoculation of Vero cells to check for bacterial contamination. Warming all medium to 37° C prior to use is favorable to the formation of a more consistent monolayer of Vero cells in the roller cultures. The roller vessels are incubated at 37° C on a roller apparatus with speed adjusted to one revolution each 2.5 minutes. Medium is changed on the roller vessels at 3–4 day intervals. Monolayers of Vero cells are established within 7–10 days, at which time the cultures are inoculated with 3–5 X $10^6$ organisms. The medium is changed after 24 hours, the monolayer washed with 25 ml fresh medium and fresh medium added. Subsequently, the media is changed twice daily for the next 10–12 days. Significant numbers of trypomastigotes appeared in the medium of these cultures 10–12 days after inoculation with parasites and can be collected by centrifugation.

EXAMPLE 3

Separation Of Cellular Antigen

For the collection of trypomastigotes, medium from four cell production roller vessels is pooled, centrifuged at 10,000 × G and washed three times with sterile Lockes' solution. The density of trypomastigotes in these cultures generally reached 15 to 20 × $10^6$ per ml of culture medium and this number of organisms is collected once or twice daily or on alternate days; thus, each cell production roller vessel produces 1.5 – 2.0 × $10^9$ trypomastigotes per day. A few amastigotes (less than 20%) also are present in the medium. Few (less than 1%) eipmastigotes were observed. The trypomastigotes can be separated from the amastigotes by the DEAE chromatographic procedure of Al-Abbassy et al. J. Parasitol. 58 (3):631 (1972).

The medium from several flasks is pooled, the parasites harvested by centrifugation at 10,000 X G in a refrigerated centrifuge (2° C) and washed three times by centrifugation with sterile Locke's solution. The parasites are subsequently stored frozen in sterile Locke's solution pH 7.2 until a desired quantity is accumulated. The organisms are subsequently sonicated at 20,000 Kc/sec in an ice bath for a total of 2 minutes (15 seconds sonication followed by 30 seconds cooling). The material is then centrifuged at 10,000 X G for 10 minutes at 2° C and the supernatant and aliquots of this material are stored frozen until ready for use. This supernate serves as the antigen for vaccination of × animals and for immunoprecipitin diagnostic procedures.

EXAMPLE 4

Immunization Of Mice Against T. Cruzi With Antigens Prepared From Trypomastigotes/Amastigotes Grown In Cell Culture Vaccination of mice with antigen prepared from *T. Cruzi* grown in cell culture (typomastigotes and amastigotes) has resulted in significant protection against challenge with *T. Cruzi* as evidenced by decreased parasitemia and mortality in the vaccinated groups. Mice were inoculated via the subcutaneous route on the back of the neck with *T. Cruzi* antigen in complete Freunds' adjuvant (total of 5 mg protein per mouse) on alternate weeks for three injections. Control groups received equivalent quantities of protein from sonicated HeLa cells only, Freunds' adjuvant alone, or saline. All mice were challenged approximately two weeks after the last injection of antigen. Parasitemia counts were made on all animals at 10 days post-infection and continued through day 33 when the blood of all experimental animals was microscopically negative from parasites.

Mice inoculated with the supernate from sonicated *T. Curzi* grown in HeLa cell cultures were observed to have significantly lower mean parasitemias 17–27 days post-infection when compared to the mean parasitemias of the control groups. There was no difference in the means parasitemias of the control groups throughout the course of acute Chagas' disease in these experiments. Mortality was reduced in the groups of animals inoculated with antigen from sonicated *T. Cruzi* from cell culture; all of the animals recovered from acute Chagas' disease while mortality in all groups ranged from 30–50%. This difference was observed as early as 24 days post-infection.

Similar results were obtained in a separate experiment similar to that discussed above except each mouse received a total of 1.5 mg of protein. Those mice receiving 3 injections of protein from sonicated trypomastigotes/amastigotes from cell culture were more resistant to subsequent challenge with *T. Cruzi* as evidence by lower maximum parasitemia and reduced mortality in these animals as compared to the control groups.

In the experiments described above it was anticipated that if protection against challenge with *T. Cruzi* were observed in vaccinated animals, the question would arise concerning the possibility that the antigen preparations contained viable parasites and the protection observed resulted from an active infection in the vaccinated animals. Blood from the vaccinated animals was cultured in NNN medium to check for the possibility of infection. Xenodiagnosis using *Rhodnius prolixus* or *Triatoma infestans* was also carried out on some of the vaccinated mice. No parasites were detected in the blood of mice injected with sonicated *T. Cruzi* by either of these procedures. The possibility of an active infection appears to be remote since culture techniques and xenodiagnosis failed to detect any infections in these animals. The vaccines are more effective than both conventional epimastigote vaccines and sonicated epimastigote supernates.

EXAMPLE 5

Diagnostic Immunoelectrophoresis in Laboratory Animals

Experimentally infected rats and mice were tested using the antigen prepared according to Example 3 and the IEOP cross-over immunoelectrophoresis system described in aforementioned U.S. Pat. No. 3,407,133. Three to four week old female $CF_1$ mice and five to six week old Cobs Albino rats were infected by intraperitoneal injection with 1×$10^6$ parasites in the epimastigote stage (the stage carried by the insect vectors of Chagas' disease), obtained according to Example 1, or 5.0×$10^4$ trypomastigotes from a donor rat or mouse.

Pre-innoculation sera were collected and samples taken weekly from two to twelve weeks post-infection.

Electrophoresis was performed by placing ten microliters of antigen having a protein concentration of 3.5 mg/ml in the wall nearest the anode, and ten microliters of undiluted serum samples in the wells nearest the cathode. A current of 40 mA was applied for 30 minutes, after which time the plates were removed and read with reflected light against a dark background or stained by conventional techniques (Williams and Chase, Methods in Immunology and Immunochemistry, Vol I and II, Academic Press, 1967 and 1968).

Visible precipitation reactions were observed with more than 50% of the sera taken from rats at 2 weeks post-infection. Precipitin lines began to appear within 10 minutes after establishing the electric field and reached maximum development after 20 to 30 minutes electrophoresis. The percentage of the sera producing visible precipitin reactions increased at 3 and 4 weeks until approximately 96% of the sera were positive at 4 weeks. This same high percentage of positives was observed from sera taken at 5 to 8 weeks. 12 of 14 sera taken at 12 weeks gave positive reactions. Sera from rats of similar age maintained as uninfected controls did not produce any visible precipitation when reacted in this system.

When these data are examined in relation to the course of parasitemia, it is apparent that the first positive reactions are observed with sera taken at about the time parasites begin to appear in the blood in significant numbers. Although parasites are generally no longer found in the blood on microscopic examination after 4 to 5 weeks post-infection, sera from the vast majority of these animals continued to yield positive reactions. Approximately 90% of the sera obtained from these animals produce positive reactions at 12 weeks when the disease is in the early chronic stage. Pooled sera collected from mice at 2, 6, and 12 weeks post-infection gave visible precipitin reactions while sera obtained from uninfected control mice produced no evidence of reaction.

As was observed in rats, the reactions produced by mouse sera are related to the course of parasitemia. The first positive reactions are observed with sera obtained from mice at about the time when the parasites are first seen in the blood in significant numbers. Parasites are not readily found in the blood of mice by microscopic examination after 5 to 6 weeks post-infection. However, pooled sera drawn from mice at 12 weeks post-infection still gave strongly positive immunoprecipitin reactions. Again, this demonstrates the efficacy of the test for detecting Chagas' disease during the early chronic stages.

EXAMPLE 6

Clinical Diagnosis of Chagas' Disease

Serum samples from a laboratory-acquired case of Chagas' disease were tested. Serum taken 7 days after the patient accidentally injected himself with mouse blood containing *T. Cruzi* failed to show any evidence of reaction. Serum taken at 19 days, at the onset of acute symptoms, however, did yield a positive reaction. At this time parasites could not be demonstrated microscopically but the blood was positive by xenodiagnosis and culture. Serum obtained from this patient at 40, 71, 99, 127, and 158 days continued to give positive reactions. No parasites could be detected in the blood sample taken from this patient at 158 days.

A total of 23 sera from individuals with Chagas' disease of unknown duration was tested and 21 gave distinct positive precipitin reactions. One of the human sera produced no evidence of reaction while one other produced a questionable result. All of these sera had passive hemagglutination (PHA) titers ranging from 1:32 to 1:4096. There was no correlation between the intensity of the reaction in IEOP and PHA titer; a number of sera with the higher PHA titers resulted in rather weak precipitin lines, while a number of those with low PHA titers resulted in very prominent precipitin lines.

EXAMPLE 7

Specificity of Antigen Preparation

Sera from 4 patients with *Leishmania braziliensis*, sera from 5 patients with *L. tropica* and sera from 9 patients with cutaneous leishmaniasis were tested with the *T. Cruzi* antigen and no evidence of reaction was observed. Neither sera from 2 patients which were VDRL-positive nor sera from 2 patients which were RA-positive showed a precipitation reaction when tested against the trypomastigote antigen in IEOP.

Antigen prepared in a similar manner from the epimastigote state of *T. Cruzi* and reacted in the cross-over electrophoresis system resulted in many false positive reactions with sera from normal animals, reacted with sera from animals and humans with leishmaniasis and reacted with only about 50% of the sera from animals and humans with known infections with *T. Cruzi*.

These tests indicate that the antigen of the present invention from *T. Cruzi* grown in Vero cell culture and consisting of up to 80% trypomastigotes is far superior to prior art preparations for use in the diagnosis of Chagas' disease in experimental animals and man. Cross-over electrophoresis and the new antigen offer a rapid, simple procedure. The sensitivity is good (greater than 90%) and the specificity is high. No cross reactions or false positives have been observed, which is in contrast to currently existing antigens and procedures which always yield some false positives and cross reactions, as has been reported by Fife in *Expt. Parasitol* 30: 132–163, (1972).

The preceding examples can be repeated with similar success by substituting the generally and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for diagnosing Chagas' disease in a living mammal susceptible to infection by *Trypanosoma cruzi* which comprises:
    a. reacting in vitro an antibody-containing blood sample from said mammal in an immunoprecipitin test with an immunologically effective amount of a purified water-soluble antigen preparation capable of forming a precipitated antigen-antibody complex in an immunoprecipitin reaction when contacted with antibodies associated with chronic Chagas' disease, said antigen preparation comprising an immunoprecipitatingly effective concentration and amount of water-soluble cellular antigens released by disruption of cells from essentially only the trypomastigote and amastigote growth stages of the protozoa *Trypanosoma cruzi* and being substantially free from serum protein antibodies, from antigens associated with the epimastigote growth stage of said protozoa and from water-insoluble cellular material; and
    b. diagnosing the presence of Chagas' disease from the formation of precipitin bands at an antigen-antibody interface.

2. The process of claim 1 wherein said immunoprecipitin test is a cross-over electrophoresis test.

3. The process of claim 2 wherein said test is an immuno-osmoelectrophoresis test.

4. The process of claim 1 wherein 60–80% of said antigen preparation is obtained from the trypomastigote growth stage of said protozoa.

5. The process of claim 4 wherein said antigen preparation is in the form of an aqueous balanced salt solution containing 0.1–10 mg. protein per ml.

* * * * *